(12) United States Patent
Vaitekunas et al.

(10) Patent No.: US 9,622,749 B2
(45) Date of Patent: Apr. 18, 2017

(54) ULTRASONIC GENERATOR SYSTEMS AND METHODS

(71) Applicant: Cybersonics, Inc., Erie, PA (US)

(72) Inventors: Jeffrey J. Vaitekunas, Erie, PA (US); Emery S. Rose, Manhasset, NY (US)

(73) Assignee: Cybersonics, Inc., Erie, PA (US)

( * ) Notice: Subject to any disclaimer, the term of this patent is extended or adjusted under 35 U.S.C. 154(b) by 0 days.

(21) Appl. No.: 15/212,135

(22) Filed: Jul. 15, 2016

(65) Prior Publication Data

US 2016/0325311 A1 Nov. 10, 2016

Related U.S. Application Data

(63) Continuation of application No. 14/037,096, filed on Sep. 25, 2013, now Pat. No. 9,504,471.

(51) Int. Cl.

| | |
|---|---|
| *H01L 41/09* | (2006.01) |
| *A61B 17/12* | (2006.01) |
| *A61B 17/22* | (2006.01) |
| *B06B 1/02* | (2006.01) |
| *B06B 1/06* | (2006.01) |
| *A61B 17/32* | (2006.01) |
| *A61B 17/00* | (2006.01) |

(52) U.S. Cl.
CPC ........ *A61B 17/12* (2013.01); *A61B 17/22012* (2013.01); *A61B 17/320068* (2013.01); *B06B 1/0253* (2013.01); *B06B 1/0269* (2013.01); *B06B 1/0276* (2013.01); *B06B 1/0614* (2013.01); *A61B 2017/0015* (2013.01); *A61B 2017/22014* (2013.01); *A61B 2017/22027* (2013.01); *B06B 2201/20* (2013.01); *B06B 2201/76* (2013.01)

(58) Field of Classification Search
CPC ................. B06B 2201/20; B06B 2201/76
USPC .................................... 310/311–371
See application file for complete search history.

(56) References Cited

U.S. PATENT DOCUMENTS

| | | | | |
|---|---|---|---|---|
| 3,293,456 | A | | 12/1966 | Shoh |
| 3,441,875 | A | * | 4/1969 | Shoh ...................... H03K 17/10 310/316.01 |
| 3,443,130 | A | * | 5/1969 | Shoh .................... B06B 1/0253 310/316.01 |
| 3,923,456 | A | * | 12/1975 | Willard, Sr. ......... A61K 8/0291 516/79 |
| 4,510,806 | A | * | 4/1985 | Janisiewicz .......... H05K 13/026 209/556 |

(Continued)

FOREIGN PATENT DOCUMENTS

| | | | | |
|---|---|---|---|---|
| EP | 0765637 | A2 * | 9/1995 | ............. A61B 17/32 |
| EP | 0765637 | B1 | 7/2004 | |

(Continued)

OTHER PUBLICATIONS

International Search Report and Written Opinion for International Application No. PCT/US2014/052691, mailed on Dec. 4, 2014, 6 pages.

*Primary Examiner* — Thomas Dougherty
(74) *Attorney, Agent, or Firm* — Ulmer & Berne LLP

(57) ABSTRACT

Embodiments shown and described herein relate, in general, to systems and methods for driving ultrasonic transducers and, more particularly, to systems and methods for controlling the output of high power ultrasonic transducers and improving performance of ultrasonic systems.

15 Claims, 10 Drawing Sheets

(56) References Cited

U.S. PATENT DOCUMENTS

| | | | | |
|---|---|---|---|---|
| 4,626,728 A | * | 12/1986 | Flachenecker | B06B 1/0253 310/316.01 |
| 4,996,674 A | * | 2/1991 | Thompson | B06B 1/0618 310/321 |
| 5,026,387 A | * | 6/1991 | Thomas | A61B 17/320068 310/316.01 |
| 5,312,329 A | * | 5/1994 | Beaty | A61B 17/320068 604/22 |
| 5,421,829 A | * | 6/1995 | Olichney | A61B 17/320068 604/22 |
| 5,447,509 A | * | 9/1995 | Mills | A61B 17/22012 600/459 |
| 5,630,420 A | * | 5/1997 | Vaitekunas | A61B 17/320068 600/459 |
| 5,672,930 A | * | 9/1997 | Narisawa | H02N 2/026 310/317 |
| 5,754,016 A | * | 5/1998 | Jovanovic | A61C 17/20 318/114 |
| 5,897,569 A | * | 4/1999 | Kellogg | A61B 17/320068 310/316.01 |
| 5,968,007 A | * | 10/1999 | Simon | A61B 17/320068 604/22 |
| 6,046,527 A | * | 4/2000 | Roopnarine | H02N 2/0095 310/323.03 |
| 6,083,191 A | * | 7/2000 | Rose | A61B 17/320068 604/22 |
| 6,165,144 A | | 12/2000 | Talish et al. | |
| 6,261,249 B1 | | 7/2001 | Talish et al. | |
| 6,355,006 B1 | | 3/2002 | Ryaby et al. | |
| 6,413,220 B1 | | 7/2002 | Rose | |
| 6,524,251 B2 | | 2/2003 | Rabiner et al. | |
| 6,524,261 B2 | | 2/2003 | Talish et al. | |
| 6,551,337 B1 | | 4/2003 | Rabiner et al. | |
| 6,636,030 B1 | | 10/2003 | Rose et al. | |
| 6,652,547 B2 | | 11/2003 | Rabiner et al. | |
| 6,660,013 B2 | | 12/2003 | Rabiner et al. | |
| 6,726,698 B2 | | 4/2004 | Cimino | |
| 6,733,451 B2 | | 5/2004 | Rabiner et al. | |
| 6,866,670 B2 | | 3/2005 | Rabiner et al. | |
| 7,494,468 B2 | | 2/2009 | Rabiner et al. | |
| 7,503,895 B2 | | 3/2009 | Rabiner et al. | |
| 7,533,830 B1 | | 5/2009 | Rose | |
| 7,554,343 B2 | | 6/2009 | Bromfield | |
| 7,614,878 B2 | | 11/2009 | Paschke et al. | |
| 8,659,208 B1 | | 2/2014 | Rose et al. | |
| 8,790,359 B2 | | 7/2014 | Rabiner et al. | |
| 9,070,856 B1 | | 6/2015 | Rose et al. | |
| 9,504,471 B2 | * | 11/2016 | Vaitekunas | A61B 17/12 |
| 2002/0107446 A1 | | 8/2002 | Rabiner et al. | |
| 2005/0043629 A1 | | 2/2005 | Rabiner et al. | |
| 2005/0096669 A1 | | 5/2005 | Rabiner et al. | |
| 2005/0143660 A1 | | 6/2005 | Rabiner et al. | |
| 2007/0035203 A1 | | 2/2007 | Bromfield | |
| 2009/0143805 A1 | | 6/2009 | Palmer et al. | |
| 2012/0125977 A1 | | 5/2012 | DeAngelis | |
| 2012/0293044 A1 | | 11/2012 | Bromfield | |
| 2014/0324066 A1 | | 10/2014 | Rabiner et al. | |
| 2015/0088154 A1 | | 3/2015 | Vaitekunas et al. | |

FOREIGN PATENT DOCUMENTS

| | | | | |
|---|---|---|---|---|
| WO | | 0124716 A1 | 4/2001 | |
| WO | | WO-0124716 A1 | * 4/2001 | A61B 17/32 |
| WO | | 2015047628 A1 | 4/2015 | |

* cited by examiner

ULTRASONIC GENERATOR SYSTEMS AND METHODS

REFERENCE TO RELATED APPLICATIONS

This application is a continuation application of U.S. patent application Ser. No. 14/037,096, filed Sep. 25, 2013, the contents of which are incorporated herein by reference.

FIELD OF THE TECHNOLOGY

Embodiment of the technology relate, in general, to systems and methods for driving ultrasonic transducers and, more particularly, to systems and methods for controlling the output of high power ultrasonic transducers and improving performance of ultrasonic systems.

BACKGROUND

Ultrasonic instruments can be advantageous because they can be used to cut and/or coagulate organic tissue using energy in the form of mechanical vibrations transmitted to a surgical end-effector at ultrasonic frequencies. Ultrasonic vibrations, when transmitted to organic tissue at suitable energy levels and using a suitable end-effector, can be used to cut, dissect, or cauterize tissue, or to break up stones, cross occlusions, dissolve blood clots or perform numerous other procedures. Ultrasonic instruments can be particularly advantageous because of the amount of ultrasonic energy that can be transmitted from the ultrasonic transducer through the waveguide to the surgical end-effector. Such instruments can be suited for use in minimally invasive procedures, such as endoscopic or laparoscopic procedures, where the end-effector can be passed through a trocar to reach the surgical site.

SUMMARY

One embodiment of a method for controlling an ultrasonic transducer can include providing a generator, providing an ultrasonic transducer having a first stack and a second stack, where the first stack can be configured to be reverse phase to the second stack such that the first stack can be in compression when the second stack is in tension, transmitting a first ultrasonic signal to the first stack with the generator, where the first ultrasonic signal can have a first frequency, and transmitting a second ultrasonic signal to the second stack with the generator, where the second ultrasonic signal can have a second frequency, where the first frequency can be different from the second frequency.

One embodiment of a method for controlling an ultrasonic transducer can include providing a generator, providing an ultrasonic transducer having a first stack and a second stack, providing a first ultrasonic signal that can have a first frequency, providing a second ultrasonic signal that can have a second frequency, where the second frequency can be different form the first frequency, summing the first ultrasonic signal and the second ultrasonic signal to create a summed signal, transmitting the summed signal to the first stack with the generator, providing a third ultrasonic signal, where the third ultrasonic signal can be inverted relative to the first ultrasonic signal, and transmitting the third ultrasonic signal to the second stack.

One embodiment of a method for controlling an ultrasonic transducer can include providing an ultrasonic transducer having a first piezoelectric stack and a second piezoelectric stack, providing a generator, where the generator can include a transformer that can have a first winding and a second winding, the first winding being wound in a direction opposite the second winding, where the first winding can be configured to provide electrical energy to the first piezoelectric stack and the second winding can be configured to provide energy to the second piezoelectric stack such that the first piezoelectric stack can be reverse phase to the second piezoelectric stack, the first piezoelectric stack can be in compression when the second piezoelectric stack is in tension, and the first piezoelectric stack can be in tension when the second piezoelectric stack is in compression. The method can include providing a first ultrasonic signal having a first frequency, providing a second ultrasonic signal having a second frequency, where the second frequency can be different form the first frequency, providing a summer, summing the first ultrasonic signal and the second ultrasonic signal with the summer to create a summed signal, transmitting the summed signal to a first amplifier, transmitting the summed signal to the first piezoelectric stack with the generator, providing an inverter that can be configured to generate a third ultrasonic signal, where the third ultrasonic signal can be inverted relative to the first ultrasonic signal, transmitting the third ultrasonic signal to a second amplifier, and transmitting the third ultrasonic signal to the second piezoelectric stack.

The above summary is not intended to describe each embodiment or every implementation contemplated. Advantages and attainments, together with a more complete understanding of the embodiments described herein, will become apparent and appreciated by referring to the following detailed description and claims taken in conjunction with the accompanying drawings.

BRIEF DESCRIPTION OF THE DRAWINGS

The present disclosure can be more readily understood from a detailed description of some example embodiments taken in conjunction with the following figures.

Figure 1:
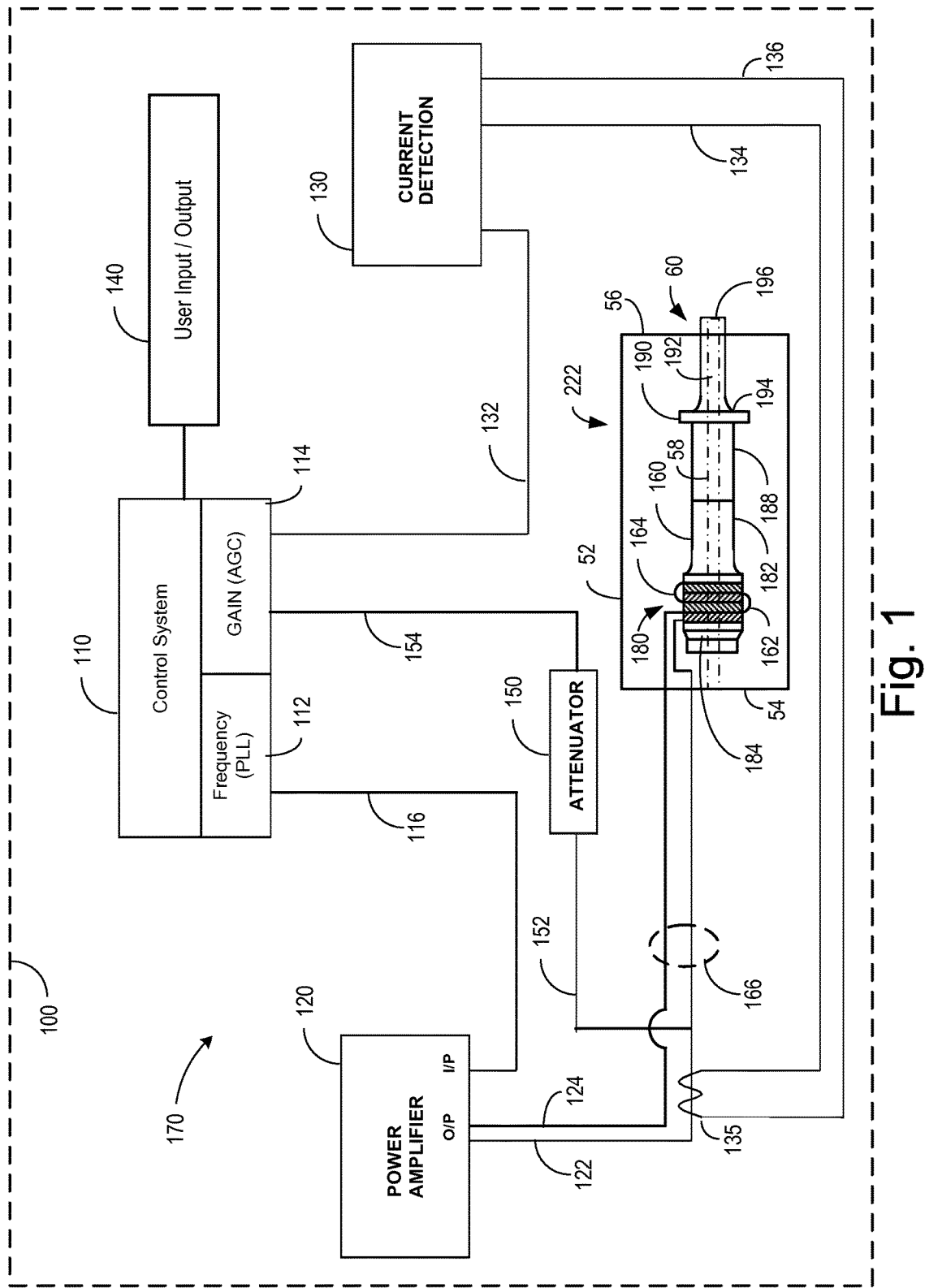
FIG. 1 is a diagrammatic view of an ultrasonic system and a plan view of a sandwich-type ultrasonic transducer according to one embodiment.

In the following description of the illustrated embodiments, references are made to the accompanying drawings, which form a part hereof, and in which is shown by way of illustration various embodiments in which the embodiments may be practiced. It is to be understood that other embodiments are contemplated, and structural and functional changes can be made without departing from the scope of the disclosure.

DETAILED DESCRIPTION

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Ultrasonic instruments in accordance with embodiments described herein can include both hollow core and solid core instruments and can be used for the safe and effective treatment of many medical conditions. Solid core ultrasonic instruments can contain solid ultrasonic waveguides that can deliver energy from a transducer to an end-effector that can be used to perform a function such as, for example, cutting or coagulating tissue, breaking up hard materials, crossing occlusions, or other surgical procedures. Solid, but flexible, wires can be used as waveguides to deliver ultrasonic energy. Hollow core ultrasonic instruments can contain ultrasonic waveguides that can deliver energy from a transducer to an end-effector that can be used to perform a function such as, for example, cutting or coagulating tissue, breaking up hard materials, crossing occlusions, and other surgical procedures, where the waveguides can have one or more channels that can, for example, be used to deliver fluids or aspirate during procedures utilizing ultrasonic energy. For example, a phacoemulsifier can have a hollow needle-like end-effector that can aspirate pieces of cataract tissue as the device breaks up a cataract.

In an example embodiment, ultrasonic vibration can be induced in the surgical end-effector by electrically exciting a transducer that can be constructed from one or more piezoelectric or magnetostrictive elements in an instrument handpiece. Vibrations generated by the transducer can be transmitted to a surgical end-effector via an ultrasonic waveguide extending from the transducer section to the end-effector.

Sandwich-type ultrasonic transducers, such as Langevin transducers, can be used for the production of high intensity ultrasonic motion. For example, a sandwich or stack of piezoelectric material positioned between metal plates can be used to generate high intensity ultrasound. Such sandwich transducers can utilize a bolted stack transducer tuned to a resonant frequency and designed to a half wavelength of the resonant frequency.

In an example embodiment, high-intensity ultrasonic transducers of the composite or sandwich type can include front and rear mass members that can include alternating annular piezoelectric elements that can include electrodes stacked therebetween. Such high-intensity transducers can be pre-stressed and can employ a compression bolt that can extend axially through the stack to place a static bias of about one-half of the compressive force that the piezoelectric transducers can tolerate. When the transducers operate, they can be configured or designed to remain in compression and can swing, for example, from a minimum compression of nominally zero to a maximum peak of no greater than the maximum compressive strength of the material.

In an example embodiment, a stud can be threadedly engaged with both the first and second resonator to provide compressive forces to a transducer stack. Threaded studs can be used for attaching and detaching transmission components to the transducer assembly. Such bolts and studs can be utilized to maintain acoustic coupling between elements of the sandwich type transducer or any attached acoustic assembly. Coupling can help maintain tuning of the assembly and can allow the assembly to be driven in resonance. Sandwich-type transducers can include relatively high Q devices, and during operation can be driven at or near resonance, and can be maintained within a relatively narrow frequency range by feedback control methods.

Example embodiments can reduce or prevent degradation of performance when placed in tortuous paths within the surgical arena. Example embodiments can be relatively easy to control, which can reduce or eliminate overshoot of amplitude and premature mechanical failure.

Systems and methods in accordance with embodiments described herein can provide for controlling the output of high power ultrasonic transducers and may improve performance of associated ultrasonic systems. Example embodiments can improve energy delivery and can control the output of high power ultrasonic transducers as energy is delivered through flexible waveguides.

FIG. 1 illustrates a diagrammatic view of one embodiment of an ultrasonic system 100 in combination with a plan view of a sandwich-type ultrasonic transducer 160. The ultrasonic transducer 160, which can be known as a "Langevin stack", can include a piezoelectric stack 180, a first resonator designated or back-mass 184, and a second resonator or front-mass 182. The ultrasonic transducer 160 can include an integral number of one-half system wavelengths (n$\lambda$/2), where n is an integer and lambda is the acoustic wavelength. For example, the ultrasonic transducer 160 illustrated in FIG. 1 can be a full-wave resonator, including two $\lambda$/2 sections, for a total acoustic length of $\lambda$, which is one full wavelength. The back-mass 184, piezoelectric stack 180, and front-mass 182 can make up one half-wavelength, and a portion 188, a mounting flange 190 and a transmission rod 192 can make up a second half-wavelength. For example, the ultrasonic transducer 160 illustrated in FIG. 1 can include portion 188, mounting flange 190, a velocity transformer 194, and a distal-end 196 that can be part of the second half-wavelength. In an alternate embodiment such components can be contained in a single half-wavelength. Distal-end 196 can be the end-effector, or can be attached to a waveguide leading to an end-effector that can be used to deliver ultrasonic energy to an object, such as tissue, plastic, metal or other object or target.

The distal end of back-mass 184 can be connected to the proximal end of stack 180, and the proximal end of front-mass 182 can be connected to the distal end of stack 180. The front-mass 182 and back-mass 184 can be fabricated from titanium, aluminum, stainless steel, or any other suitable material such as materials having a high Q value. Front-mass 182 and back-mass 184 can have a length determined by a number of variables, including the thickness of the stack 180, the density and modulus of elasticity of materials used for back-mass 184 and front-mass 182, and the resonant frequency of the ultrasonic transducer 160. The front-mass 182 can be tapered inwardly from its proximal end to its distal end to amplify the ultrasonic vibration amplitude as velocity transformer 194, or alternately can have no amplification.

The stack 180 of the ultrasonic transducer 160 can include a piezoelectric section of alternating positive electrodes 162 and negative electrodes 164, with piezoelectric elements alternating between the electrodes 162 and 164. The piezoelectric elements can be fabricated from any suitable material, such as, for example, lead zirconate-titanate, lead meta-niobate, lead titanate, or other piezoelectric crystal material. Each of the positive electrodes 162, negative electrodes 164, and piezoelectric elements can have a bore extending through the center thereof. The positive and negative electrodes 162 and 164 can be electrically coupled to wires 124 and 122, respectively. Wires 124 and 122 can be encased within a cable 166 and can be electrically connectable to a generator 170 of an ultrasonic system 100.

Referring still to FIG. 1, the ultrasonic transducer 160 can convert the electrical signal from the generator 170 into mechanical energy that can result in vibratory motion of the ultrasonic transducer 160, and any attached end-effector, at ultrasonic frequencies. When the ultrasonic transducer 160 is energized, a vibratory motion standing wave can be generated through the ultrasonic transducer 160. The amplitude of the vibratory motion at any point along the ultrasonic transducer 160 can depend on the location along the ultrasonic transducer 160 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength ($\lambda$/4).

Distal end 196 at the distal end of the ultrasonic transducer 160 can be placed in contact with tissue of the patient to transfer the ultrasonic energy to the tissue. The cells of the tissue in contact with the distal end 196 of the ultrasonic transducer 160 can be affected by the distal end 196. As the distal end 196 engages the tissue, for example, thermal energy or heat can be generated as a result of internal cellular friction within the tissue. The heat can be sufficient to break protein hydrogen bonds, which can cause the highly structured protein (e.g., collagen and muscle protein) to denature or otherwise become less organized. As the proteins are denatured, a sticky coagulum can form to seal or coagulate small blood vessels such as when the coagulum is below 100° C. Deep coagulation of larger blood vessels can result when the effect is prolonged.

The transfer of the ultrasonic energy to the tissue can cause other effects including mechanical tearing, cutting, cavitation, cell disruption, and emulsification. The amount of cutting as well as the degree of coagulation obtained can vary with the vibrational amplitude of the distal end 196, the amount of pressure applied by the user, and the sharpness of the distal-end 196. The distal end 196 of the ultrasonic transducer 160 can focus the vibrational energy onto tissue in contact with the distal end 196, and can intensify and localize thermal and mechanical energy delivery.

Generator 170 can include a control system 110 that can include a frequency control loop 112 and a gain control loop 114 that can provide for automatic frequency tracking and automatic gain control respectively, based on feedback loop as further described herein. An ultrasonic frequency signal 116 can be provided to a power amplifier 120 that can be used to drive the piezoelectric stack 180. The input (I/P) of the power amplifier 120 can amplify the ultrasonic frequency signal 116 before delivering the amplified signal output (O/P) to the piezoelectric stack 180 using wire 122 as a positive designated signal and wire 124 as a negative designated signal. The positive designated signal wire 122 can be coupled to an attenuator 150 via a high voltage signal wire 152. The attenuator can reduce the high voltage signal to an attenuated level (1/100 for example) that can be measured by the gain control loop 114, which can be coupled to the attenuator 150 by low voltage signal wire 154. The gain control loop 114 can be connected to a current detection portion 130 via a current level signal wire 132. The current detection portion 130 can determine the current being delivered from the power amplifier 120 to the piezoelectric stack 180 using a current sensor 135 connected by wires 134, 136 to the current detection portion 130.

The ultrasonic generator can include a user input/output 140 that can provide function information to a user such as power level, fault information, system status, or other useful information. The user input/output 140 can also provide for user input to the ultrasonic generator 170 such as desired power level or other desired control or use functional information.

Figure 2:
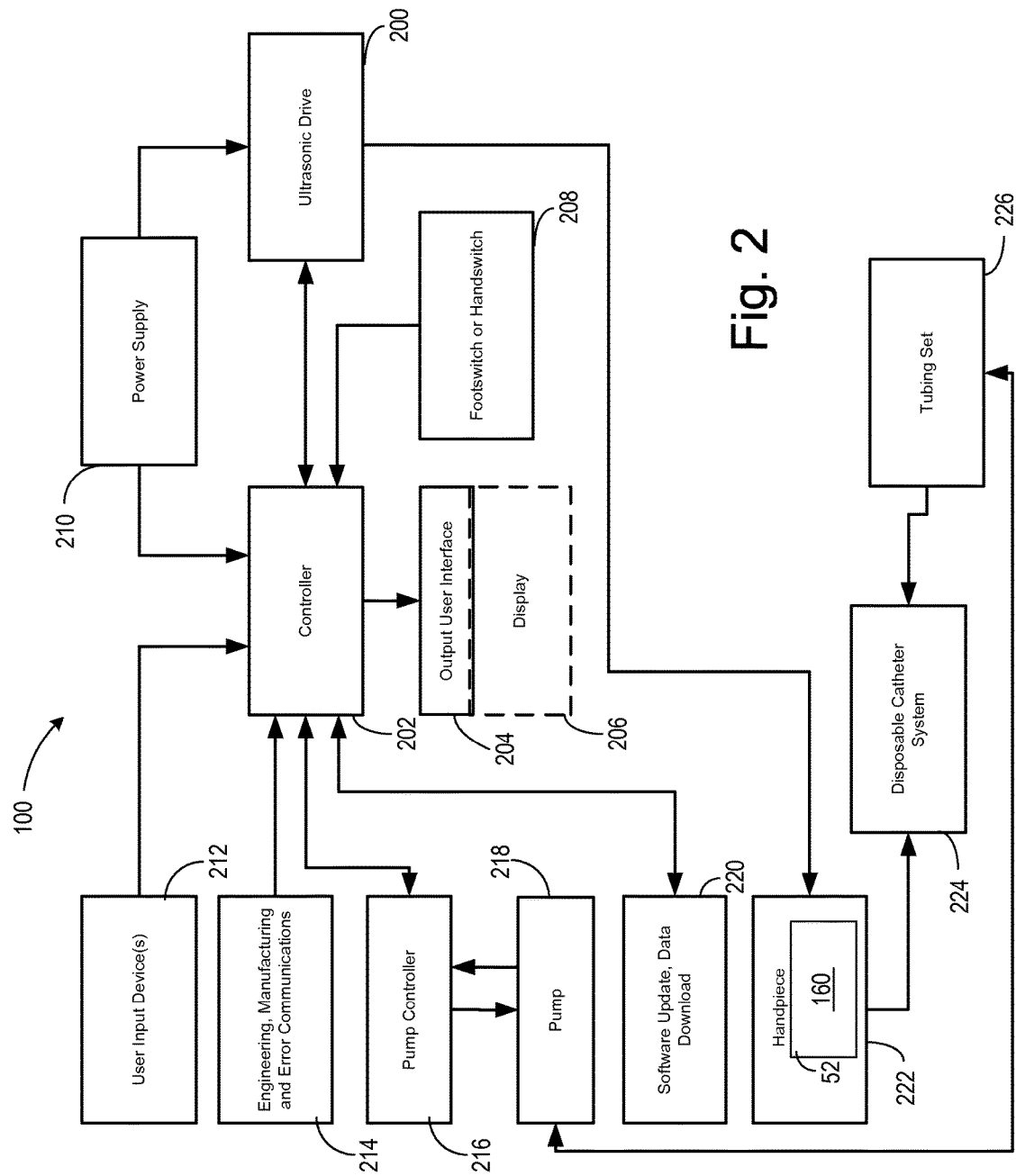
FIG. 2 is a functional block diagram of an ultrasonic system according to one embodiment.

FIG. 2 illustrates a functional block diagram of the ultrasonic system 100 including the generator 170 according to one embodiment. Referring to both FIG. 1 and FIG. 2, when the generator 170 is activated via a footswitch or handswitch 208, electrical energy can be continuously applied by the generator 170 to stack 180 of the ultrasonic transducer 160. A phase-lock-loop in a controller 202 of the generator 170 can monitor feedback from the ultrasonic transducer 160 as will be described in more detail herein.

The phase-lock-loop can adjust the frequency of the electrical energy sent by the generator 170 to match one or more preselected harmonic frequencies of the ultrasonic transducer 160. In addition, a second feedback loop, for example the automatic gain control 114, in the control system 110 can maintain the electrical current supplied to the ultrasonic transducer 160 at one or more preselected levels. These preselected levels can help achieve substantially constant vibrational amplitude at the distal end 196 of the ultrasonic transducer 160 at one or more frequencies of operation and/or one or more modulation schemes. The phase-lock-loop and current control loop can be non-orthogonal, such that changing one can affect the other.

The electrical signal supplied to the ultrasonic transducer 160 can cause the distal end 196 (FIG. 1) to vibrate longitudinally in the range of, for example, from about 20 kHz to about 500 kHz, from about 20 kHz to about 150 kHz, or at any other suitable level of vibration. The amplitude of the acoustic vibrations at the distal end 196 can be controlled, for example, by controlling the amplitude of the electrical signal applied to the stack 180 of the ultrasonic transducer 160 by the generator 170.

As noted above, the footswitch or handswitch 208 of the generator 170 can allow a user to activate the generator 170 so that electrical energy can be continuously supplied to the ultrasonic transducer 160. Continuous supply of energy to the generator 170 can include both continuous wave ultrasonic frequency delivery of energy, and also modulated supply of energy, such as amplitude modulation, frequency modulation, or pulse width modulation schemes, as well as combinations thereof. In an example embodiment, the footswitch or handswitch 208 can include a foot activated switch that can be detachably coupled or attached to the generator 170 by a cable or cord. In an alternate embodiment, a hand switch can be incorporated in a handpiece assembly 222 and can allow the generator 170 to be activated by a user, for example, by pushing a button (not shown) on the transducer housing.

The generator 170 can also include a power supply 210 that can include a power line for insertion in an electrosurgical unit or conventional electrical outlet. It is contemplated that the generator 170 can also be powered by a direct current (DC) source, such as a battery.

Referring still to FIGS. 1 and 2, the handpiece assembly 222 can include a multi-piece housing 52 or outer casing that can be configured to retain the ultrasonic transducer 160 such that the operator can be isolated from the vibrations of the ultrasonic transducer 160. The housing 52 can be substantially cylindrical in shape and can be configured to be held by a user, where any suitable shape and size is contemplated. The housing 52 can be multi-piece, a single component, or a unitary construction.

The housing 52 of the handpiece assembly 222 can be constructed from a durable plastic, such as polysulfone or PTFE. It is also contemplated that the housing 52 can be made from a variety of materials, such as high impact polystyrene, liquid crystal polymer, polypropylene, or the like.

Referring to FIG. 1, the handpiece assembly 222 can include a proximal end 54, a distal end 56, and can define a centrally disposed axial opening or cavity 58 extending longitudinally therein. The distal end 56 of the handpiece assembly 222 can include an opening 60 that can be configured to allow the ultrasonic transducer 160 of the ultrasonic system 100 to extend therethrough, and the proximal end 54 of the handpiece assembly 222 can be connected to the generator 170 by cable 166.

The mounting flange 190 can be positioned near a node of vibration and can be adjacent a velocity transformer 194, where the velocity transformer 194 can function to amplify the ultrasonic vibratory motion that can be transmitted through the ultrasonic transducer 160 to the distal end 196. In an example embodiment, the velocity transformer 194 can include a solid tapered horn. As ultrasonic energy is transmitted through the velocity transformer 194, the velocity of the acoustic wave can be transmitted through the velocity transformer 194 and can be amplified. It is contemplated that the velocity transformer 194 can be any suitable shape, such as, for example, a stepped horn, a conical horn, an exponential horn, a unitary gain horn, or any other suitable horn design.

The transmission rod 192 can, for example, have a length substantially equal to an integral number of one-half system wavelengths (n$\lambda$/2). The transmission rod 192 can be constructed from a solid core shaft constructed out of material that can propagate ultrasonic energy efficiently, such as titanium alloy (i.e., Ti-6Al-4V), a nickel-titanium alloy (Nitinol), or an aluminum alloy. It is contemplated that the transmission rod 192 can be constructed from any other suitable material, can be hollow or solid core, and can be a flexible wire. The transmission rod 192 can also amplify the mechanical vibrations that can be transmitted through the transmission rod 192 to the distal end 196.

It is also contemplated that the distal end 196 can have a surface treatment (not shown) that can improve the delivery of energy and can provide the desired tissue effect. For example, all or a portion of the distal end 196 can be micro-finished, coated, plated, etched, grit-blasted, roughened, or scored to enhance coagulation in tissue or to reduce adherence of tissue and blood to the end effector. Additionally, the distal end 196 can be sharpened or shaped such that the energy transmission characteristics can be enhanced. For example, the distal end 196 can be blade-shaped, hook-shaped, or ball-shaped.

In an example embodiment, the components of ultrasonic transducer 160 can be acoustically coupled. The distal end of the ultrasonic transducer 160 can be acoustically coupled to the proximal end of an ultrasonic end-effector by, for example, a threaded connection such as a stud or threaded bore.

Referring now to FIG. 2, the generator 170 can include a controller 202 that can be integral to the generator 170, a power supply 210, and can include a footswitch or handswitch 208. When activated by the footswitch or handswitch 208, the generator 170 can provide energy to drive the ultrasonic transducer 160 of the ultrasonic system 100 at a predetermined frequency and can drive the distal end 196 (FIG. 1) at one or more predetermined vibrational frequencies or amplitude levels. The generator 170 can drive or excite the ultrasonic transducer 160 at or near any suitable resonant frequency of the ultrasonic transducer 160.

The block diagram of FIG. 2 includes an example of the generator 170 of the ultrasonic system 100. The generator 170 can include a controller 202, where the controller 202 can be a programmed microprocessor which can, for example, be a MOTOROLA model number 68HC11. The controller 202 can be programmed to monitor appropriate power parameters and vibratory frequency and can provide an appropriate power level in various operating modes.

In general, it will be apparent to one of ordinary skill in the art that at least some of the embodiments described herein can be implemented in many different embodiments of software, firmware, and/or hardware. The software and firmware code can be executed by a processor, controller, or any other similar computing device. The software code or specialized control hardware that can be used to implement embodiments is not limiting. For example, embodiments described herein can be implemented in computer software using any suitable computer software language type, using, for example, conventional or object-oriented techniques. Such software can be stored on any type of suitable computer-readable medium or media, such as, for example, a magnetic or optical storage medium. The operation and behavior of the embodiments can be described without specific reference to specific software code or specialized hardware components. The absence of such specific references is feasible, because it is clearly understood that artisans of ordinary skill would be able to design software and control hardware to implement the embodiments based on the present description with no more than reasonable effort and without undue experimentation.

Moreover, the processes described herein can be executed by programmable equipment, such as computers or computer systems and/or processors. Software that can cause programmable equipment to execute processes can be stored in any storage device, such as, for example, a computer system (nonvolatile) memory, an optical disk, magnetic tape, or magnetic disk. Furthermore, at least some of the processes can be programmed when the computer system or controller is manufactured or stored on various types of computer-readable media.

It can also be appreciated that certain portions of the processes described herein can be performed using instructions stored on a computer-readable medium or media that direct a computer system to perform the process steps. A computer-readable medium can include, for example, memory devices such as diskettes, compact discs (CDs), digital versatile discs (DVDs), optical disk drives, or hard disk drives. A computer-readable medium can also include memory storage that is physical, virtual, permanent, temporary, semi-permanent, and/or semi-temporary.

A "controller," "computer," "computer system," "host," "server," or "processor" can be, for example and without limitation, a processor, microcomputer, minicomputer, server, mainframe, laptop, personal data assistant (PDA), wireless e-mail device, cellular phone, pager, processor, fax machine, scanner, or any other programmable device configured to transmit and/or receive data over a network. Computer systems and computer-based devices disclosed herein can include memory for storing certain software modules used in obtaining, processing, and communicating information. It can be appreciated that such memory can be internal or external with respect to operation of the disclosed embodiments. The memory can also include any means for storing software, including a hard disk, an optical disk, floppy disk, ROM (read only memory), RAM (random access memory), PROM (programmable ROM), EEPROM (electrically erasable PROM) and/or other computer-readable media. Non-transitory computer-readable media, as used herein, comprises all computer-readable media except for a transitory, propagating signals.

Manually operable controls can be provided as user input devices 212 for the purpose of, for example, enabling an operator to adjust the power level to be applied to the transducer assembly when operating. In one embodiment, simultaneous cutting and small vessel coagulation of a predetermined level can be obtained whenever the distal end 196 is in contact with tissue. It is also contemplated that controls can be voice activated, wirelessly transmitted signals, touch-screens, or other input/output devices.

The user input devices 212 may include, without limitation, keyboard entry, writing from pen, stylus, finger, or the like, with a computer mouse, or other forms of input (voice recognition, etc.). The user input devices 212 can include a tablet, desktop, phone, board, or paper. In one embodiment, the user may interact with the ultrasonic system 100 by writing with a smart pen on normal paper, modified paper, or a hard flat surface of their preference. In this embodiment, the user may receive real-time feedback, or at least near real-time feedback, or may synchronize with a controller 202 at a later date. The ultrasonic system 100 can include a personal computer or one or multiple computers in server-type system.

The generator 170 can include an ultrasonic drive 200 which can be coupled to the ultrasonic transducer 160 through a matching network. In operation, the ultrasonic drive 200 can supply electrical energy to the ultrasonic transducer 160 by way of a matching network (not shown) and an isolation transformer (not shown). Frequency control for generating output signals from the generator 170, corresponding to a resonant frequency of the ultrasonic transducer 160 (carried by the handpiece assembly 222), can be produced through the use of a phase-lock-loop 112 (FIG. 1) which can include a phase detector (not shown) and oscillator (not shown). The phase detector can compare the phase of the output driving current and voltage signals with an error signal obtained from an error amplifier (not shown) used to control the voltage controlled oscillator to produce the desired output frequency.

The computer or controller 202 can be software updatable using a software update and data download capability 220. The software update, data download capability 220 can be used to program the controller 202 at the time of manufacture, or as software updates are available. It is also contemplated that an engineering, manufacturing and error communications system 214 can log errors or operational information that can be transmitted and/or stored for tracking usage, tracking hours of run-time, tracking error rates, tracking malfunctions, or providing other data for engineering, manufacturing or business purposes. An output user interface 204 can be provided that can optionally include a display 206. The display 206 can also include a user input device 212, such as a touch-screen display.

The handpiece assembly 222 can be used to drive the distal end 196 (FIG. 1), which can be at the end of an elongated catheter, for example. A disposable catheter system 224 can be removably connectable to the handpiece assembly 222 and can drive the distal end 196 within the vascular system. The ultrasonic system 100 can include a pump 218, a pump controller 216, and a tubing set 226 and can provide controlled flow of fluid within the disposable catheter system 224 for cooling or lubrication purposes or for the delivery of physician-specified fluids.

Figure 3:
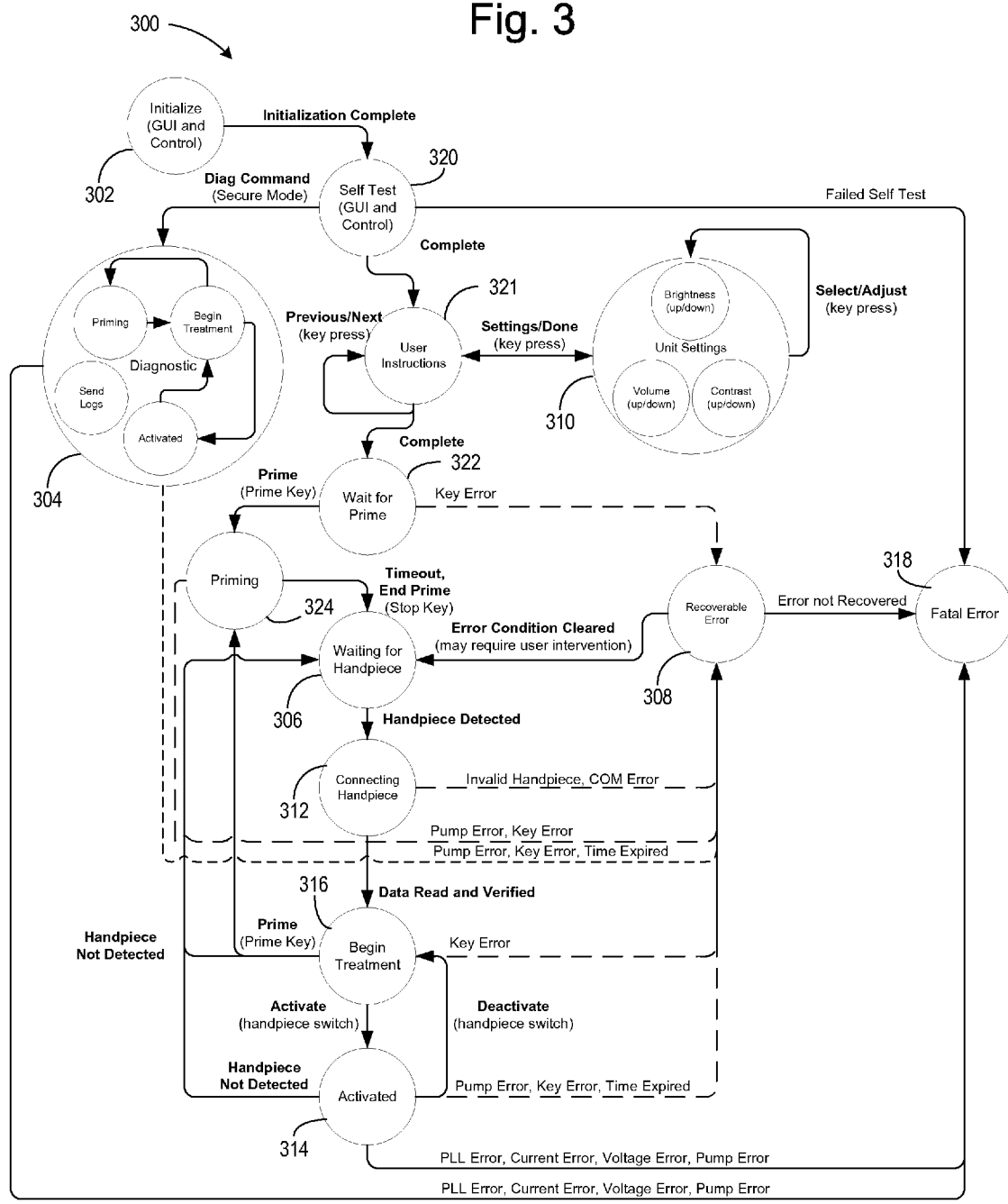
FIG. 3 is a flowchart of a control scheme for an ultrasonic system according to one embodiment.

FIG. 3 is a flowchart of a control scheme 300 for an ultrasonic system in accordance with one embodiment. An initialization step 302 can be used, for example, to power up the components in the generator in a particular order. For example, the controller (e.g., controller 202) can be powered first such that software has time to load and take control of adjustable parameters before power is provided to the power amplifier (e.g. power amplifier 120). A self-test step 320 can be completed, for example, to check that the software was loaded successfully and is functioning, and to make sure that the appropriate power is applied to the appropriate components. A user instruction step 321 can be used to provide user instructions such as, for example, instructing the user how to assemble a device, how to attach tubing and/or fluid containers, how to incorporate pharmaceuticals, or other useful instructions. In response to a key press if a key-pad is provided, in response to completion of the instruction step 321, or other desirable initiation, a select/adjust step 310 can optionally be provided to, for example, adjust brightness of a display, adjust volume of a buzzer or speaker, adjust contrast, or other useful selection or adjustment.

When the optional user instruction step 321 or self-test step 320 is completed, a wait state 322 can be entered if some user action is required to continue operation. A recoverable error state 308 can be entered if, for example, a timeout occurs, a software error is detected, a user error is detected, or other recoverable error occurs. If a fatal error 318 occurs, the ultrasonic system 100 can be shut down, can display an error message, can provide an error tone, or other fatal error action or combination of actions can be performed. In embodiments incorporating fluid pumps, flow detectors, bubble detectors, or other fluid management schemes, a priming step 324 can automatically or manually occur. When priming step 324 is completed the ultrasonic system 100 can enter into a waiting for handpiece step 306.

A connecting handpiece step 312 can be used to detect the connection of a handpiece (e.g., handpiece 222), determine characteristics of an already connected handpiece, adjust settings in the generator 170 to control a particular handpiece, diagnose the condition of a handpiece, or other desirable action. Fatal or non-fatal errors can be detected and can send the ultrasonic system 100 into the recoverable error 308 or fatal error 318 states, or can enter into a diagnostic 304 state. The diagnostic 304 state can be used to diagnose errors, determine criticality of errors, determine condition of transducers (e.g., transducer 160) or associated end-effectors or waveguides, log errors, or other desirable diagnostic action.

If the ultrasonic system 100 is determined to be in adequate condition to function, a begin treatment step 316 can be performed, where ultrasonic energy can be delivered. Fatal or non-fatal errors can be detected and send the ultrasonic system 100 into the recoverable error 308 or fatal error 318 states, or can enter into a diagnostic 304 state, where energy can be turned off or left on depending on the type of error that occurs. Errors can be indicated to the user or logged in an error log as determined by the controller (e.g., controller 202). As the ultrasonic system 100 is activated 314, continuous or occasional monitoring of parameters and errors can occur and appropriate actions can be implemented. For example, the ultrasonic system 100 can be providing energy even though the phased-lock-loop is not locked onto the operating frequency, while the diagnostic step 304 attempts to regain lock. After, for example, ten attempts to lock onto the transducer resonant frequency, the diagnostic step 304 can send the ultrasonic system 100 into the fatal error 318 mode, where energy delivery can be interrupted.

Figure 4:
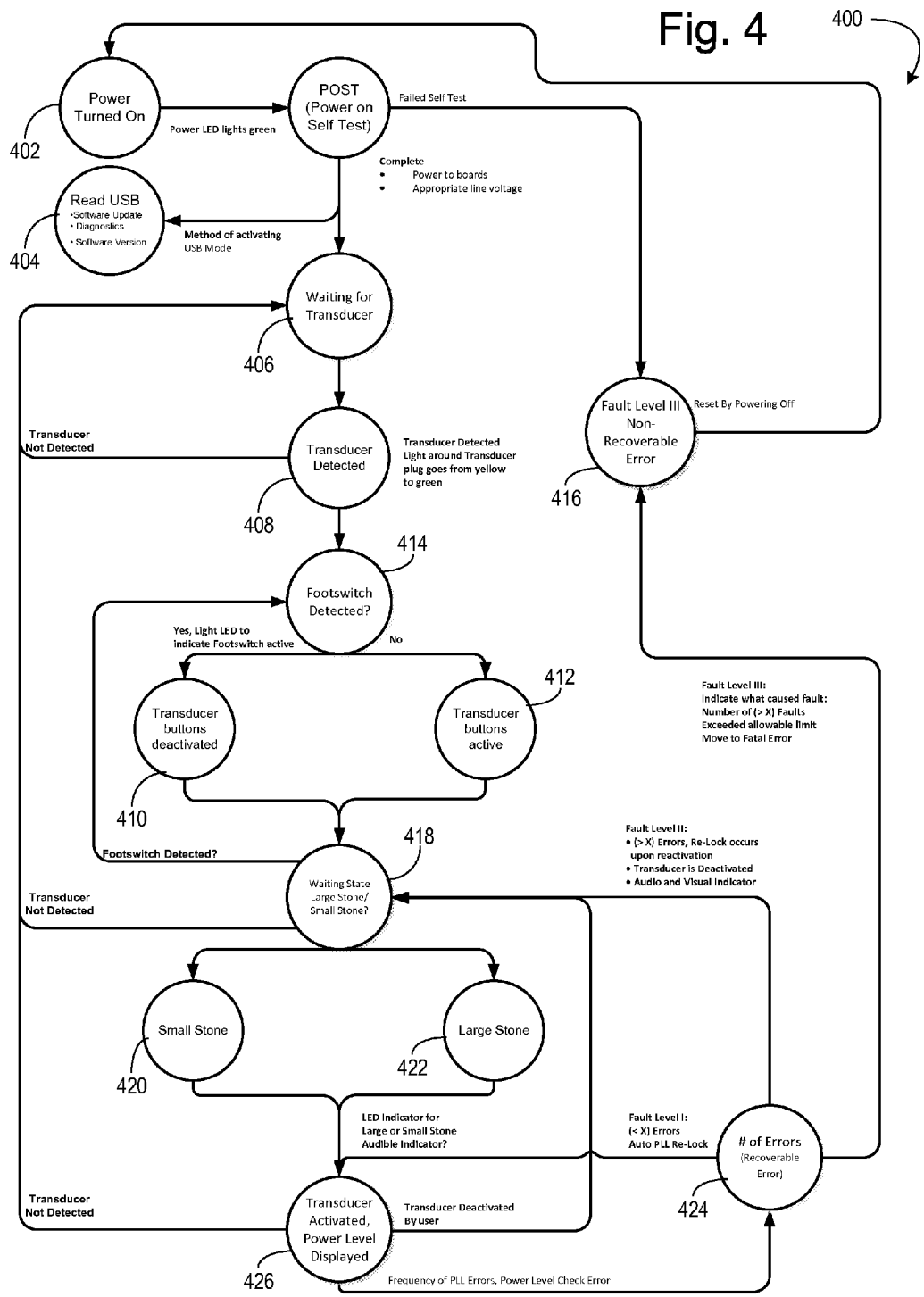
FIG. 4 is a flowchart of a control scheme for an ultrasonic system according to an alternate embodiment.

FIG. 4 is a flowchart of one embodiment of a control scheme 400 for an ultrasonic system 100. In the example control scheme 400 illustrated in FIG. 4, the power turned on step 402 can occur from the push of an on/off switch by a user. A power-on self test 403 can be performed. If, for example, a dongle (not shown) is attached to a USB port (not shown) on the ultrasonic system 100, a read USB step 404 can be performed to, for example, perform a software update, perform a diagnostic program located on the USB dongle, identify a software version, download an error log, or other desirable input or output using the USB connection. A wait state 406 can be maintained until/unless a transducer (e.g., transducer 160) is connected to the ultrasonic system 100. A transducer connected state 408 can initiate a feedback to the user, such as, for example, where a light (not shown) around the transducer plug lights up or changes color. If a footswitch (e.g., footswitch 208) is available and desired, a footswitch detected state 414 can initiate changes to the system such as, for example, deactivating transducer buttons 410 if transducer switches are available. If no footswitch is connected, a transducer buttons active step 412 can test for button connections, can enable or disable system features, or can provide for other desired actions. A wait step 418 can include waiting for button or footswitch actuation, watching for errors, or performing other system checks and/or adjustments. Upon actuation by a user, a first operating mode 420 or a second operating mode 422 can be entered. The first operating mode 420 can be, for example, operating the ultrasonic system 100 in a small stone mode for an ultrasonic lithotripsy procedure, operating the ultrasonic system 100 in a first frequency mode for an ultrasonic blood clot dissolving procedure, operating the ultrasonic system 100 in a dual-frequency mode for an ultrasonic lithotripsy procedure, or other desirable operating mode. The second operating mode 422 can be, for example, operating the ultrasonic system 100 in large stone mode for an ultrasonic lithotripsy procedure, operating the ultrasonic system 100 in a second frequency mode for an ultrasonic blood clot dissolving procedure, toggling the system between multiple operating modes, or other desirable actions. System output functional information can be provided to the user as output user interface 204 output (FIG. 2), for example, at output step 426. A transducer-activated indication light (not shown) can light up on the front panel of ultrasonic system 100, a power-level display can display output power, a tone can indicate energy delivery, or other desirable system functions can occur. A number of errors 424 can be recorded, and upon exceeding a predetermined number of errors, a non-recoverable error state 416 can be entered, where the system can be shut down and the user can be forced to cycle the power to attempt to use the system again. Upon re-start, the ultrasonic system 100 can use a log of errors to perform additional diagnostics or to display particular information to the user, such as, for example, informing the user to return the system for repair.

Figure 5:
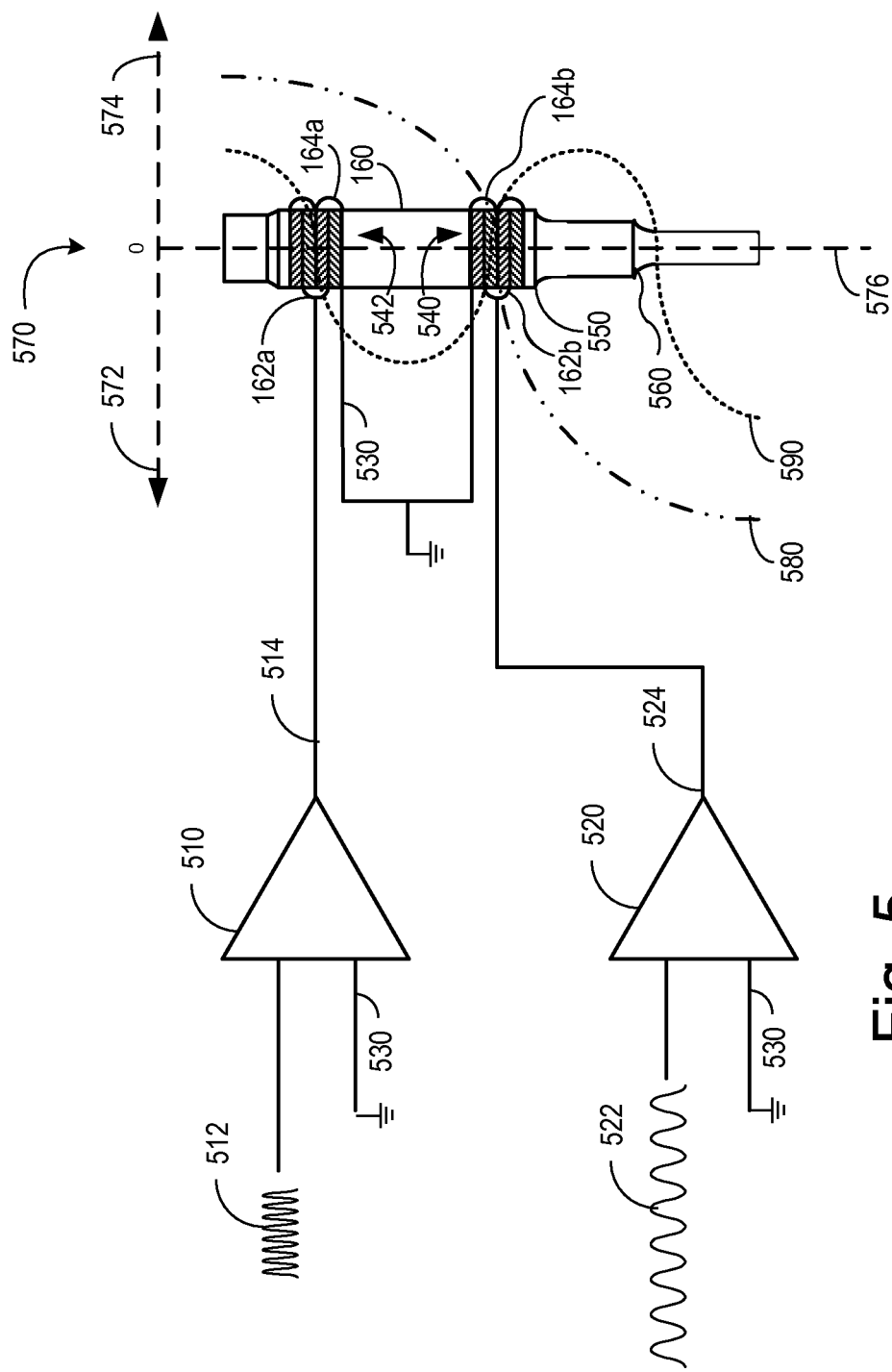
FIG. 5 is a diagrammatic view of an ultrasonic system and a plan view of a sandwich-type transducer according to an alternate embodiment, where the ultrasonic system is shown driving the transducer at multiple frequencies.

FIG. 5 is a schematic and plan drawing illustrating a system and method for driving a transducer at multiple frequencies using an ultrasonic system according to one embodiment. One embodiment of a control scheme 500 for a multi-frequency transducer 570 can include a longitudinal axis 576 with the origin of the longitudinal axis 576 identified at 0, and extending from the proximal end of the multi-frequency transducer 570 (near point 0) through to the distal end of the multi-frequency transducer 570. As illustrated, a positive axis 574 and a negative axis 572 can be normal to the longitudinal axis 576. The positive axis 574 can indicate a relative amount of displacement in a positive direction and the negative axis 572 can indicate a relative amount of displacement in a negative direction. A first curve 580 can indicate the relative displacement at each location along the longitudinal axis 576 of transducer 570 due to a first frequency of vibration. A second curve 590 can indicate the relative displacement at each location along the longitudinal axis 576 of transducer 570 due to a second frequency of vibration. The first and second frequencies can simultaneously be present, such that the displacement at any point on the multi-frequency transducer 570 can be the sum of all simultaneously occurring vibrations.

An example embodiment of the transducer 570 can include a first stack 540 and a second stack 542. Referring to FIG. 5, the first curve 580 can indicate a displacement of zero at the center of the first stack 540, which can indicate that the first frequency of vibration is the fundamental resonant frequency of the longitudinal resonance of transducer 570 corresponding to a wavelength of λ/2. The second curve 590 can indicate a displacement of zero at the center of the first stack 540 and a displacement of zero at the location of the center of the second stack 542, which can indicate that the second frequency of vibration is the third harmonic resonant frequency of the longitudinal resonance of transducer 570 corresponding to a wavelength of 3λ/2. Any odd harmonics of the ultrasonic transducer 160 can be driven concurrently or individually.

The first stack 540 can include positive electrodes 162b that can be electrically connected to an amplifier 520 using wire 524. The second stack 542 can include positive electrodes 162a that can be electrically connected to an amplifier 510 using wire 514. Using the arrangement illustrated in FIG. 5, each stack can be driven independently at one or more different frequencies. The multi-frequency transducer 570 can have a common ground 530 for all components, although any suitable configuration is contemplated. Amplifier 520 can receive a first frequency input signal 522, can amplify the first frequency input signal 522, and can deliver the amplified signal to stack 540. For illustration purposes, the first frequency input signal 522 can have a lower frequency than a second frequency input signal 512. The second frequency input signal 512 can be amplified by amplifier 510, whose amplified signal can drive stack 542. In the case where the first frequency input signal 522 is the fundamental frequency of the multi-frequency transducer 570, and the second frequency input signal 512 is the third harmonic of the multi-frequency transducer 570, the multi-frequency transducer 570 can vibrate simultaneously at both frequencies as illustrated in FIG. 5 by first curve 580 and second curve 590.

Referring to FIG. 5, the center of the second stack 542 can correspond to a node of the displacement curve 590. As illustrated, the proximal side of the second stack 542 can show positive displacement and the distal side of the second stack 542 can show negative displacement on the second curve 590. This arrangement of displacement can put the second stack 542 in compression. The second curve 590 can illustrate the displacement at a single instant of time. One half-cycle later, for example, the proximal side of the second stack 542 can show negative displacement and the distal side of the second stack 542 can show positive displacement on curve 590. The displacements can reciprocate, for example, for every cycle of the second frequency input signal 512. In an example embodiment, the first stack 540 can be reverse phase to the second stack 542, such that when the second stack 542 is in compression the first stack 540 is in tension, and vice-versa. When the multi-frequency transducer 570 is vibrating at, for example, the third harmonic as shown by second curve 590, the first stack 540 can be compressed and expanded by the second frequency input 512. Because piezoelectric elements can work as both drivers and receivers, the third harmonic signal can be driven by the first stack 540 into the output of the amplifier 520. This can induce undesired heating, disturb the control system of the generator 170 (FIG. 2), or cause other undesirable consequences. Similarly, second stack 542 can be driven by first curve 580, which may induce undesired heating, disturb the control system of the generator 170, or cause other undesirable consequences. It will be appreciated that any suitable system, such as a control system 600 (FIG. 6) can be used to mitigate such undesirable consequences. It will be appreciated that systems and methods described herein can use a single generator or a plurality of generators.

Figure 6:
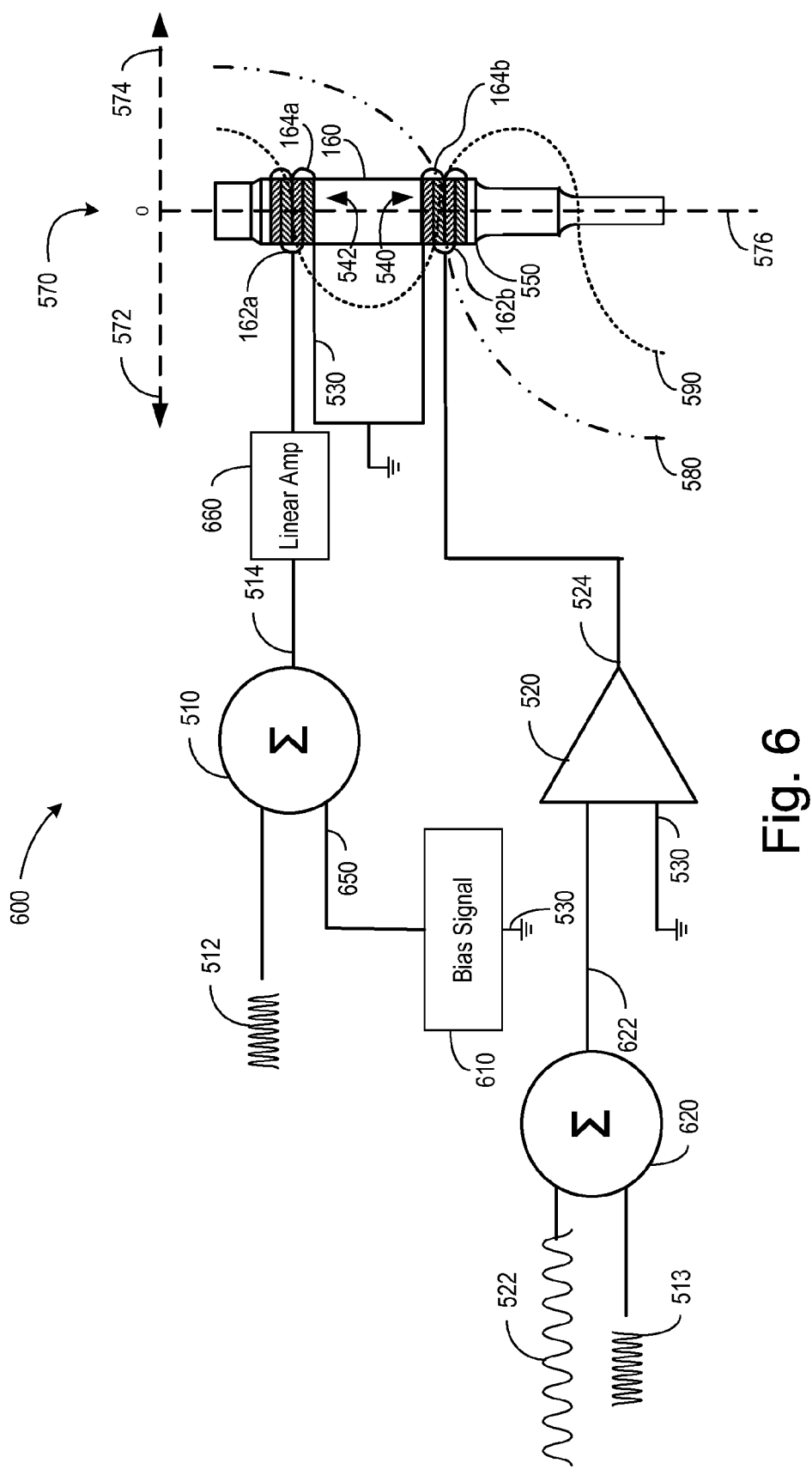
FIG. 6 is a diagrammatic view of an ultrasonic system and a plan view of a sandwich-type transducer according to an alternate embodiment, where the ultrasonic system is shown driving the transducer at multiple frequencies.

FIG. 6 depicts an alternate embodiment for driving a multi-frequency transducer 570 at multiple frequencies using an ultrasonic system. A control scheme 600 can provide correction for undesired heating, disturbing of the control system of the generator 170 (FIG. 1), or other undesirable consequences from driving an multi-frequency transducer 570 at multiple frequencies using multiple stacks (first stack 540 and second stack 542, for example.) The amplifier 520 in FIG. 6 can be driven by a summer 620. A summer output 622 can be the sum of a first ultrasonic frequency 522 and the inverse signal 513 of the second ultrasonic frequency 512. Both first stack 540 and second stack 542 can be at nodes of the third harmonic depicted by second curve 590, where the stacks 540, 542 can be out of phase, such that driving the first stack 540 with the inverse signal 513 of the second stack 542 can eliminate undesired heating, or other undesirable consequences, and can also help drive the multi-frequency transducer 570 at the desired second frequency.

Both first stack 540 and second stack 542, as illustrated in the example embodiment, can be offset from nodes of the fundamental resonant frequency as depicted by curve 580, such that the inverse of the first frequency input signal 522 may not be the desirable signal to drive the second stack 542 to reduce or eliminate heating, disturbing of the control system of the generator 170 (FIG. 1), or other undesirable consequences. A bias signal 610 can be provided to the amplifier 510 that can reduce or eliminate undesired heating, disturbing of the control system of the generator 170, or other undesirable consequences. The bias signal 610 can be the signal produced by the second stack 542 when the second stack 542 is measured in an open circuit condition as it is being driven by the transducer 160 running at the fundamental resonant frequency. Alternately, the voltage signal generated by the second stack 542 can be calculated from the applied strain due to the first curve 580. The bias signal 610 can be input to a differential input 650 of the amplifier 510, or can be input to a summer (not shown) similar to the method described using summer 620 to drive the amplifier 520.

Bias signal 610 can also include a DC component, which can be used to drive the positive electrodes 162a such that a bias stress can be placed on second stack 542. In this way, the first stack 540 and the second stack 542 can have a static bias stress from the inherent Langevin stack design, but the second stack 542 can have an additional bias static stress from the DC signal 610. The bias signal 610 can include both a DC component to supply a static pre-stress on second stack 542 and the dynamic bias stress signal associated with the stress induced by the first curve 580. This arrangement can facilitate not only the reduction or elimination of undesired heating, disturbing of the control system of the generator 170, or other undesirable consequences, but can also be used to provide that the common ground 530 is able to be maintained for both amplifier 520 and 510. For example, the sum of displacements from the second ultrasonic frequency 512 and the first ultrasonic frequency 522 may exceed the static pre-stress in the ultrasonic transducer 160. As the amplitude of the second ultrasonic frequency 512 is increased or decreased by the controller 202, the DC component of the bias signal 610 can be changed to compensate, and can help assure that the second stack 542 is always in compression throughout its dynamic excursions. In another embodiment, as the amplitude of the second ultrasonic frequency 512 is increased or decreased by the controller 202, the DC component of the bias signal 610 can be changed to compensate, and can help assure that the common ground 530 is maintained by the amplifier 510 and the amplifier 520.

Figure 7:
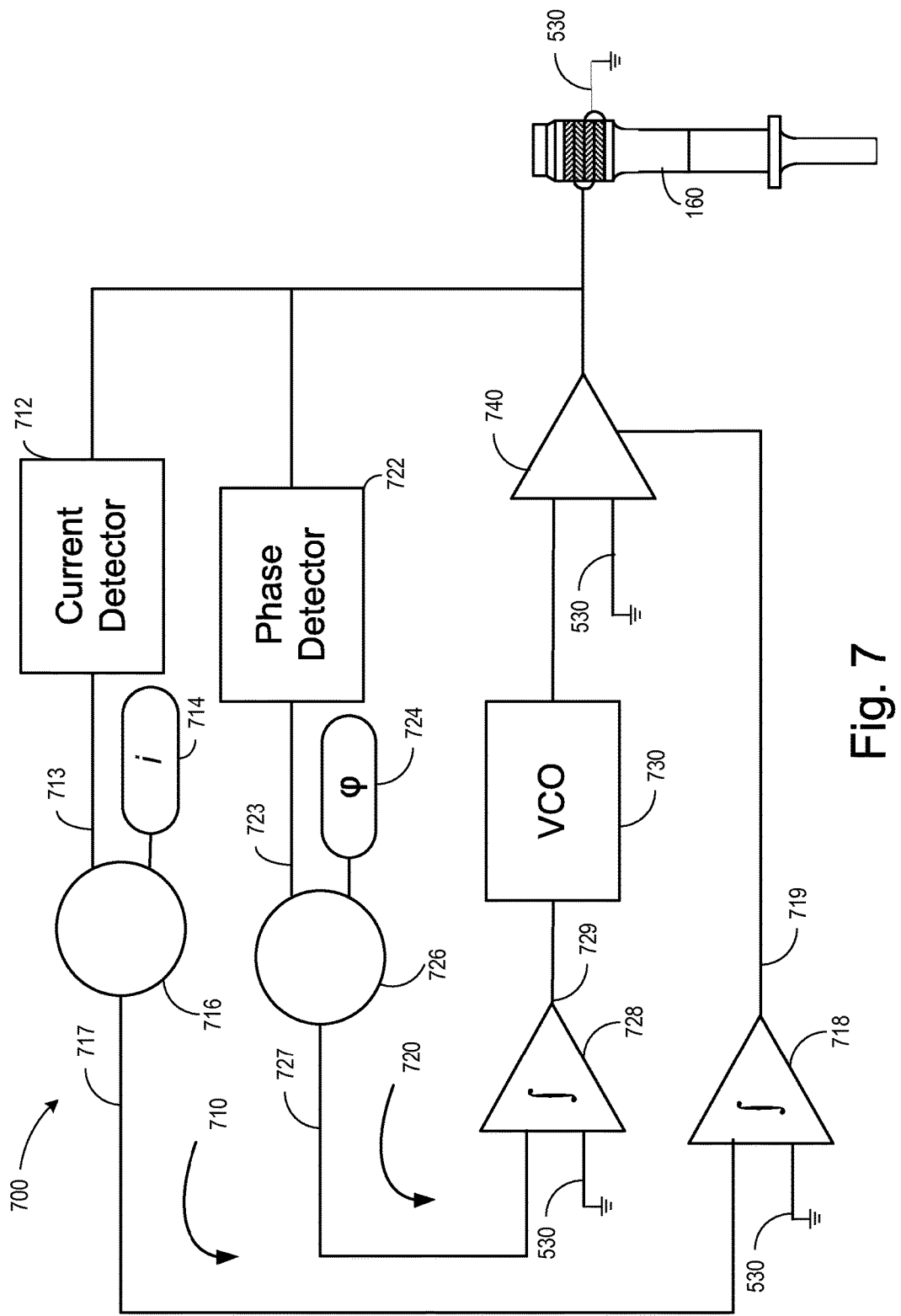
FIG. 7 is a diagrammatic view of an ultrasonic system and a plan view of a sandwich-type transducer according to an alternate embodiment, where the ultrasonic system is shown controlling the transducer at multiple frequencies.

FIG. 7 depicts an example embodiment of a control system 700 that can be used for controlling the transducer 160 at multiple frequencies. The generator 170 (FIG. 1) can include a phase detector 722 that can determine a current system phase 723. An error amplifier 726 can compare the current system phase 723 with a desired phase set-point 724, and can provide a phase error signal 727 to a cascade compensator, such as a loop cascade compensator 728, where the loop cascade compensator 728 can be referenced to the common ground 530. The loop cascade compensator 728 can provide a desired operating frequency signal 729 to a voltage controlled oscillator 730, which can drive a power amplifier 740 and can determine the frequency of the output signal from the power amplifier 740, but not the amplitude of the output signal from the power amplifier 740.

The generator 170 can include a current detector 712 that can determine a system amplitude 713 if the transducer 160 is run near series-resonance where current is proportional to amplitude. A error amplifier 716 can compare the current system amplitude 713 with a desired amplitude set-point 714, and can provide an amplitude error signal 717 to an integrator 718, where the integrator 718 can be referenced to the common ground 530. The integrator 718 can provide a desired operating amplitude signal 719 to the power amplifier 740, and can determine the amplitude of the output signal from the power amplifier 740, but not the frequency of the output signal from the power amplifier 740. Amplitude modulation of the power amplifier 740 can be controlled by adjusting the rails of a power supply providing power to an H-bridge or other amplifier topology in response to the desired operating amplitude signal 719.

The control system 700 can be implemented for each frequency that it is desired to run a transducer. For example, a current control loop 710 and a phase control loop 720 can be implemented for each frequency that the ultrasonic transducer 160 runs at simultaneously. For example, if the ultrasonic transducer 160 is designed to run at the fundamental and third harmonic as illustrated in FIG. 5, two phase control loops 720 and two current control loops 710 can be implemented to drive the first stack 540 and the second stack 542 simultaneously, tracking and controlling phase and amplitude at both frequencies using amplifier 510 and amplifier 520. It is also contemplated to use a single first stack 540, running at two frequencies simultaneously using two phase control loops 720 and two current control loops 710. It is further contemplated to use a single first stack 540, running at two frequencies simultaneously using one phase control loop 720 and one current control loop 710, and driving the first stack 540 at the second frequency where the second frequency can be a pre-determined proportion of the first frequency and the second amplitude can be a pre-determined proportion of the first amplitude.

Figure 8:
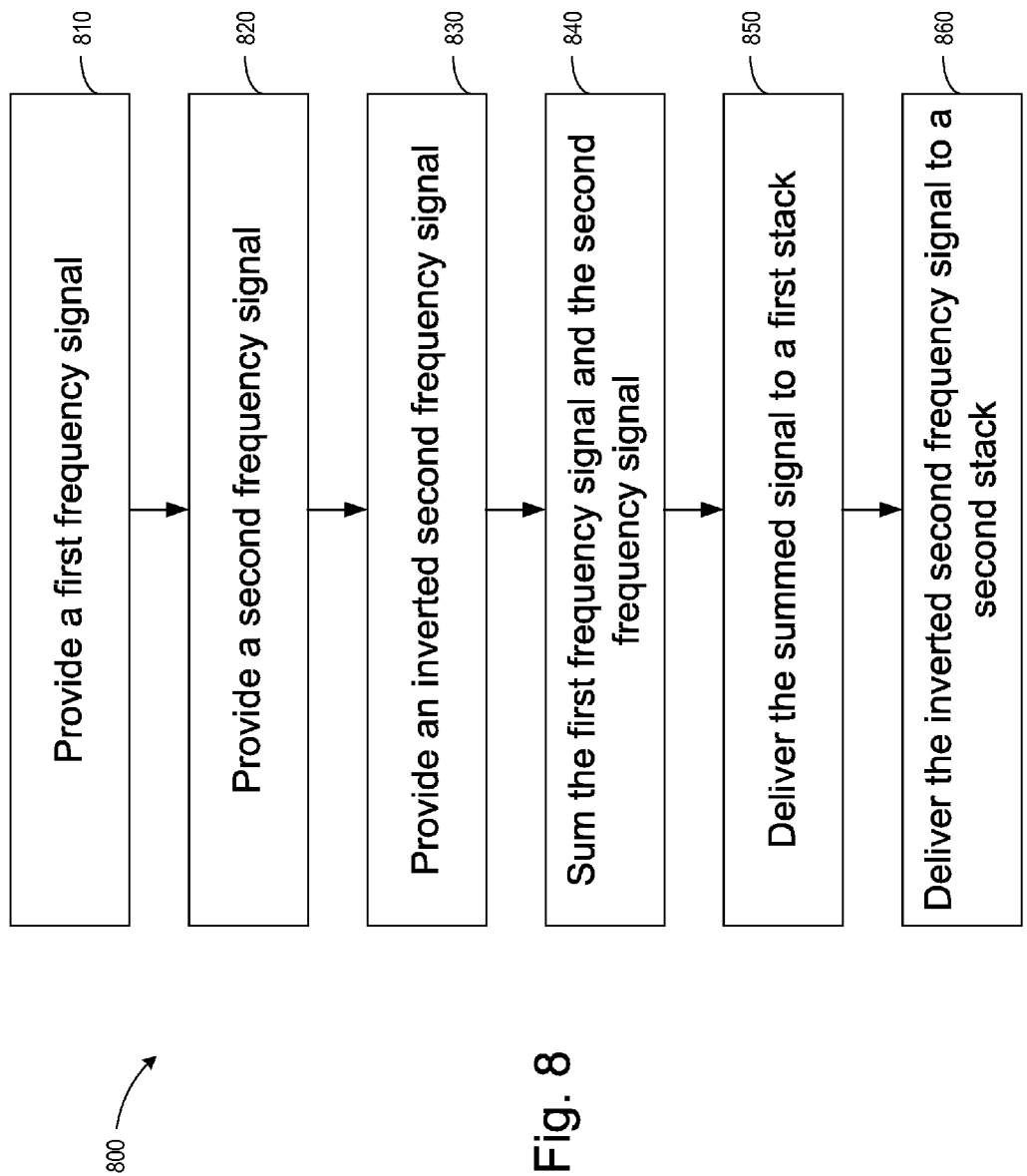
FIG. 8 is a flowchart of a method for providing multiple frequencies to a transducer according to one embodiment.

FIG. 8 depicts a method 800 according to one embodiment. The method 800 can include the steps of providing a first frequency ultrasonic signal 810, providing a second frequency ultrasonic signal 820, providing an inverted second frequency ultrasonic signal 830, summing the first frequency ultrasonic signal and the second frequency ultrasonic signal 840, such that a summed signal is produce, delivering the summed signal to a first ultrasonic stack of a transducer 850, and delivering the inverted second frequency ultrasonic signal to a second ultrasonic stack of the transducer 860.

With ultrasonic systems that have anomalous operation such as a long ultrasonically driven wire or driven masses that put mechanical shocks into the system, the phase feedback may, under certain circumstances of use, become erratic causing the analog system to loose lock. Referring to FIG. 1, the control system 110 can instantaneously detect the phase of the current and voltage. The control system 110 can include a very high resolution edge detector with a time stamp for each edge detection detected by a digital signal processor (DSP) or microcomputer.

For example, the current detection 130 can provide a current signal into the edge detection circuitry of the control system 110 as well as provide current feedback to the gain control loop 114. Also the attenuated voltage 154 can provide a voltage signal into the edge detection circuitry of the control system 110 as well as provide voltage feedback to the gain control loop 114.

Figure 9:
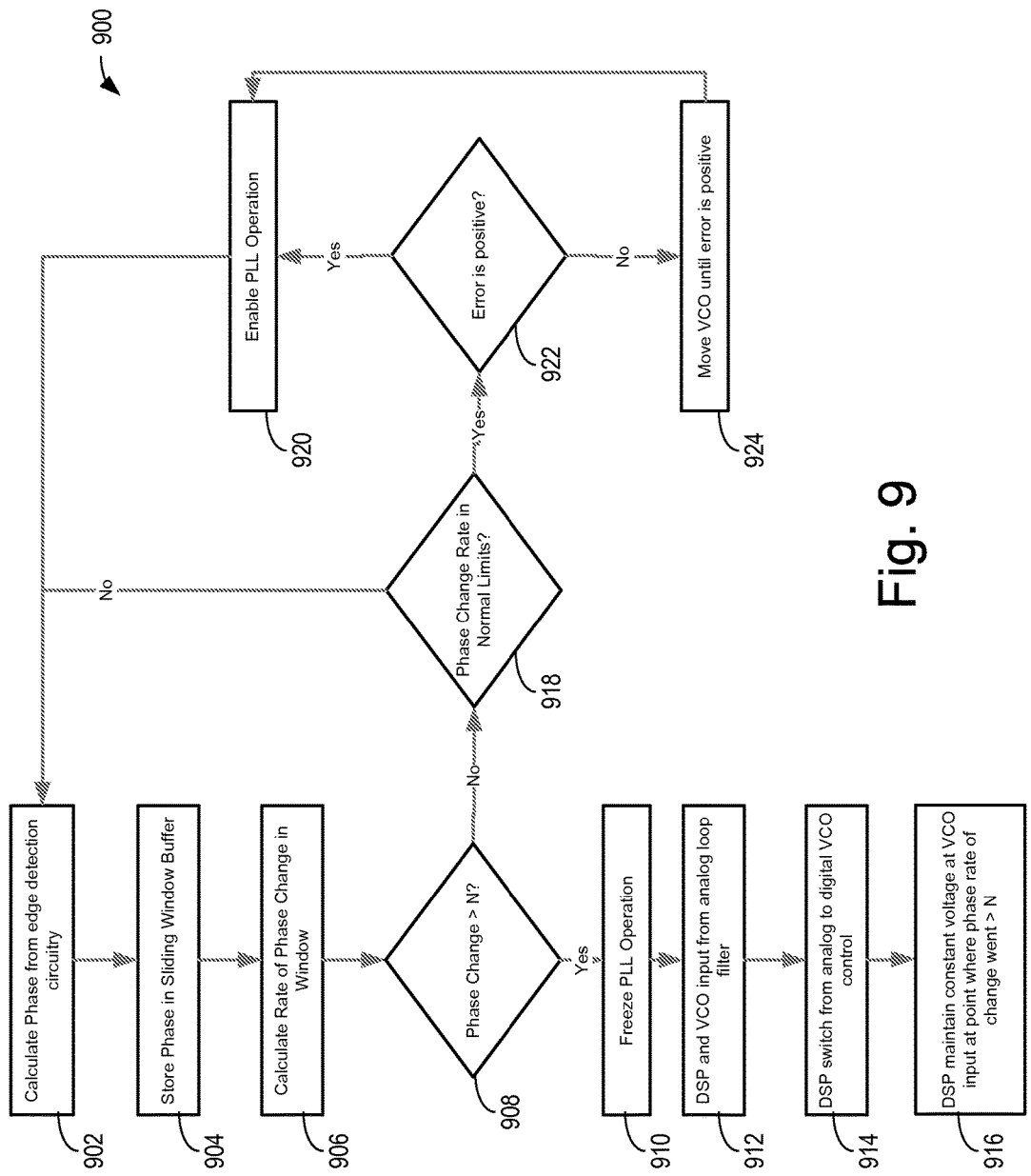
FIG. 9 is a flowchart of a method for an ultrasonic system according to one embodiment.

Referring now to FIGS. 1-9, the control system 110, which can have both instantaneous current and Voltage signals, can be capable of determining Voltage information, current information, and phase information between Voltage and current. With reference to FIG. 9, the ultrasonic system 100 (FIG. 1), using the edge detection circuitry available in a DSP, for example, can implement an algorithm 900. In algorithm 900, the DSP can detect the phase of the instantaneous current and instantaneous voltage at step 902. The DSP can then determine the phase angle between current and voltage at any instant by comparing the time stamps of detected edges of current and voltage as one skilled in the art could appreciate. The DSP can be a supervisor of an analog phase-lock-loop, and allows the analog phase-lock-loop to run the system while constantly monitoring the system phase. The system phase is necessarily delayed by averaging and filtering by the separate phase detector of the analog phase-lock-loop.

The DSP can store the phase information in a buffer, such as, for example, a sliding window buffer 904. The advantage of the DSP supervisor is that it can detect the onset of anomalous phase information very fast relative to the analog control system time constant. For example, the DSP can calculate the rate of change of phase between Voltage and Current 906 in the sliding window buffer 904. When the DSP detects the anomalous phase response, such as when a rate of change of phase exceeds a predetermined threshold 908, it can freeze the operation of the analog control loop 910 until the feedback is once again stable.

One method of detection is the maintenance of the sliding window of phase 904, and to look at the rate of change 906. If the rate of change of phase 906 exceeds the predetermined limit, the DSP can take control of the phase-lock-loop 914 and then perform error correction or stabilization before returning control back to the phase-lock-loop 920. After Freezing PLL operation 910, the DSP can take control of the voltage controlled oscillator (VCO) from the analog loop filter 912. The DSP can control a switch, such as a solid state switch, to switch the input of the VCO to, for example, a D/A converter output from the DSP. The DSP can monitor the VCO input value, and use the VCO value from right before the phase change rate>N step 908 identified a possible analomous operation of the system 100.

If in step 908, the rate of change of phase is not greater than the predetermined limit, and the phase change rate is within normal limits 918, then the DSP can check if the loop error is positive 922. If the loop error is positive then the system could be re-enabled for PLL operation 920 by, for example, switching the PLL error signal back into the VCO. If the error 922 is not positive, then the DSP could move the VCO input 924 until a positive error condition is detected at step 922, and then the PLL enabling operation 920 could occur.

Figure 10:
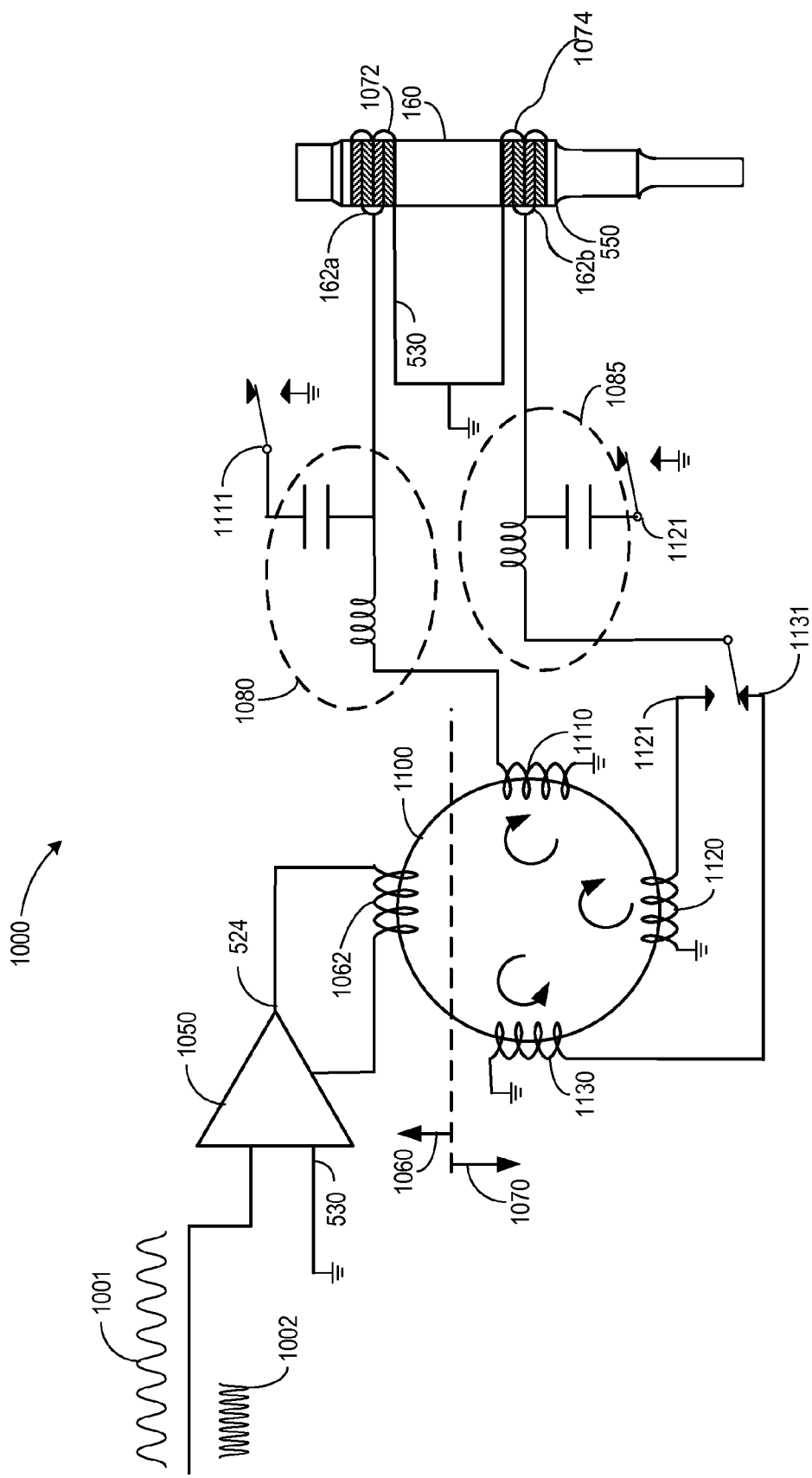
FIG. 10 is a diagrammatic view of an ultrasonic system and a plan view of a sandwich-type transducer according to an alternate embodiment, where the ultrasonic system is shown driving the transducer at multiple frequencies.

With reference to FIG. 10, an ultrasonic system 1000 can include a control system 110 (see FIGS. 1 and 2) that can be configured to drive a multi-frequency transducer 570 with a power amp 1050, a transformer 1100 with the power amp 1050 attached to a primary winding 1062 on a primary side 1060 of the transformer 1100, a pair of secondary windings 1110, 1120 on a secondary side 1070 of the transformer 1100 that can drive each of two piezo stacks 1072, 1074 in the vibrating transducer 160 assembly through impedance matching circuitry 1080 and 1085 respectively, which may include an inductor and one or more capacitors. The secondary windings 1120, 1130 of the transformer 1100 can communicate with the piezo stack 1074 through switch 1131. A third secondary winding 1130 can also communicate, through the switch 1131, with one of the piezo stacks 1074 through matching circuitry 1085, and can be wound on the transformer 1100 core in a direction opposite from the other two secondary windings 1110, 1120 to apply voltage to the piezo stack. The oppositely wound secondary winding 1130 can drive the piezo stack 1074 at a vibration mode(s) excited by driving in opposite senses. Other vibration modes can be excited by using switches 1111, 1121 to drive two or more piezo stacks 1072, 1074 in the vibrating transducer 160 with the same driving signal sense.

The system can apply electro-mechanical (ultrasonic) energy for a period of time in the order of an inertial ring up/down time constant of a resonant electro-mechanical (ultrasonic) assembly at one of a plurality of resonances of the assembly, after which energy at one of the other resonances can be applied for a similar time constant. A sum of the vibration due to applied energy, and the energy of the prior vibrational mode at the prior resonance still excited due to inertia can result in a fourier composite vibrational mode. This composite mode can modulate at the aforementioned time constant/period.

The system can include, for example, a computing system to sense resonance by either a phase-lock-loop detection, or by detecting ring down frequencies after power is disconnected in one of two or more frequency operating modes. Example systems can utilize a combination of the two methods to start at a frequency slightly below the last frequency detected on ring down for phase-lock-loop capture for maximum capture/lock speed in switching back and forth between operating frequencies. (Also high to low if parallel resonance is used instead of series resonance, starting above the last frequency detected.)

It is understood that the components and functionality depicted in the figures and described herein may be implemented in hardware, software, or a combination of hardware and software. It is further understood that the components and functionality depicted as separate or discrete blocks/elements in the figures may be implemented in combination with other components and functionality, and that the depiction of such components and functionality in individual or integral form is for purposes of clarity of explanation, and not of limitation.

Illustrations of method steps, such as, for example, the steps illustrated in FIG. 8, show steps sequentially and in a particular order. There is no need to perform the steps in the order illustrated. Deviating from the illustrated order for some or all of the steps is contemplated by the inventor, and does not depart from the scope of the present invention.

Each feature disclosed in this specification (including any accompanying claims, abstract, and drawings), may be replaced by alternative features having the same, equivalent or similar purpose, unless expressly stated otherwise. Thus, unless expressly stated otherwise, each feature disclosed is one example only of a generic series of equivalent or similar features.

While preferred embodiments of the present invention have been shown and described herein, it will be obvious to those skilled in the art that such embodiments are provided by way of example only. Numerous variations, changes, and substitutions will be apparent to those skilled in the art without departing from the invention. Accordingly, it is intended that the invention be limited only by the scope of the appended claims.

What is claimed is:

1. A method for controlling an ultrasonic transducer comprising:
providing a generator;
providing an ultrasonic transducer having a first stack and a second stack;
providing a first ultrasonic signal having a first frequency;
providing a second ultrasonic signal having a second frequency, wherein the second frequency is different from the first frequency;
summing the first ultrasonic signal and the second ultrasonic signal to create a summed signal;
transmitting the summed signal to the first stack with the generator;
providing a third ultrasonic signal, wherein the third ultrasonic signal is inverted relative to the first ultrasonic signal; and
transmitting the third ultrasonic signal to the second stack.

2. The method of claim 1, wherein the first frequency is at about a fundamental resonant frequency of the transducer and the second frequency is at about a third harmonic resonant frequency of the transducer.

3. The method of claim 1, wherein the first stack and the second stack are driven independently.

4. The method of claim 1, wherein the first stack and the second stack are configured to be in phase when the transducer is driven at the first frequency.

5. The method of claim 1, further comprising the steps of amplifying the summed signal with a first amplifier and amplifying the third ultrasonic signal with a second amplifier.

6. The method of claim 1, wherein the first stack is reverse phase to the second stack such that the first stack is in compression when the second stack is in tension, and the first stack is in tension when the second stack is in compression.

7. The method of claim 1, wherein the generator comprises a transformer having a first winding and a second winding, the first winding being wound in a direction opposite the second winding, wherein the first winding is configured to drive the first stack and the second winding is configured to drive the second stack.

8. The method of claim 7, wherein the generator comprises a third winding associated with the second ultrasonic signal.

9. The method of claim 1 wherein the third ultrasonic signal comprises a second frequency that is inverted relative to the first frequency and wherein the first frequency is not inverted.

10. A method for controlling an ultrasonic transducer comprising:
providing an ultrasonic transducer having a first piezoelectric stack and a second piezoelectric stack;

providing a generator, wherein the generator comprises a transformer having a first winding and a second winding, the first winding being wound in a direction opposite the second winding, wherein the first winding is configured to provide electrical energy to the first piezoelectric stack and the second winding is configured to provide energy to the second piezoelectric stack such that the first piezoelectric stack is reverse phase to the second piezoelectric stack, the first piezoelectric stack is in compression when the second piezoelectric stack is in tension, and the first piezoelectric stack is in tension when the second piezoelectric stack is in compression;

providing a first ultrasonic signal having a first frequency;

providing a second ultrasonic signal having a second frequency, wherein the second frequency is different from the first frequency;

providing a summer;

summing the first ultrasonic signal and the second ultrasonic signal with the summer to create a summed signal;

transmitting the summed signal to a first amplifier;

transmitting the summed signal to the first piezoelectric stack with the generator;

transmitting the third ultrasonic signal to a second amplifier; and transmitting the third ultrasonic signal to the second piezoelectric stack.

11. The method of claim 10, wherein the first ultrasonic signal is at about a fundamental resonant frequency of the ultrasonic transducer and the second ultrasonic signal is at about a third harmonic resonant frequency of the ultrasonic transducer.

12. The method of claim 10, wherein the first piezoelectric stack and the second piezoelectric stack are configured to be driven independently.

13. The method of claim 10, wherein the first stack and the second stack are configured to be in phase when the ultrasonic transducer is driven at the first frequency.

14. The method of claim 10, wherein the second amplifier comprises a bias signal input configured to bias the third ultrasonic signal.

15. The method of claim 14, wherein the bias signal is proportional to the first ultrasonic signal.

* * * * *